United States Patent [19]

Hutchings

[11] Patent Number: 4,861,514
[45] Date of Patent: Aug. 29, 1989

[54] COMPOSITIONS CONTAINING CHLORINE DIOXIDE AND THEIR PREPARATION

[75] Inventor: Richard S. Hutchings, Cincinnati, Ohio

[73] Assignee: The Drackett Company, New York, N.Y.

[21] Appl. No.: 204,065

[22] Filed: Jun. 8, 1988

[51] Int. Cl.[4] .................. A01N 59/00; C11D 3/48; C01B 11/02; D06L 3/08
[52] U.S. Cl. .................. 252/187.21; 252/187.23; 252/95; 252/106; 252/174.11; 252/103; 423/477
[58] Field of Search .................. 252/187.21, 187.22, 252/187.23; 423/477

[56] References Cited

U.S. PATENT DOCUMENTS

| | | | |
|---|---|---|---|
| Re. 31,779 | 12/1984 | Alliger | 252/187.23 |
| 2,974,001 | 3/1961 | Windbichler | 252/187.21 X |
| 4,104,190 | 8/1978 | Hartshorn | 252/187.21 |
| 4,585,482 | 4/1986 | Tice et al. | 252/187.21 X |
| 4,708,821 | 11/1987 | Shimokawa et al. | 252/187.21 X |
| 4,722,802 | 2/1988 | Hutchings et al. | 252/174 |
| 4,731,192 | 3/1988 | Kenjo et al. | 252/95 |
| 4,790,950 | 12/1988 | Hutchings | 252/102 |

OTHER PUBLICATIONS

W. J. Masschelein, *Chlorine Dioxide*, Ed. Rip G. Rice, Ann Arbor Science, Ann Arbor, Mich., 1979, pp. 67, 68, and 82–85.
R. G. Rice and J. A. Cotruvo, Eds., *Ozone/Chlorine Dioxide Oxidation*, 1978, Ozone Press Int'l, pp. 334 and 336–338.
George C. White, *Handbook of Chlorination*, 1972, Von Nostrand Reinhold, p. 597.

*Primary Examiner*—Stephen J. Lechert, Jr.
*Assistant Examiner*—Virginia B. Caress
*Attorney, Agent, or Firm*—Sandra M. Person; Charles J. Zeller

[57] ABSTRACT

A chlorine dioxide-containing composition comprising sodium chlorite; an initiator selected from the group consisting of (A) a thickening agent; (B) a colorant, (C) a perfume and mixtures thereof; chlorine dioxide at an antimicrobial concentration, and water, the sodium chlorite and the initiator being present in the composition in an amount adapted to form interactively said antimicrobial chlorine oxide concentration, said composition having a viscosity suitable to maintain the thus-formed chlorine dioxide at a steady-state concentration.

21 Claims, No Drawings

COMPOSITIONS CONTAINING CHLORINE DIOXIDE AND THEIR PREPARATION

FIELD OF INVENTION

The present invention relates to compositions containing chlorine dioxide. More specifically, the present invention concerns chlorine dioxide formation in compositions containing sodium chlorite and an initiator, the compositions having a viscosity suitable for suspendably retaining the gaseous chlorine dioxide formed subsequent to composition preparation.

BACKGROUND OF INVENTION

Chlorine dioxide is a well-known disinfecting and sterilizing agent. However, chlorine dioxide, because it is gaseous at room temperature and atmospheric pressure, has not achieved widespread use except where its gaseous nature can be used to effect, for example, in the treatment of water supplies.

U.S. Pat. No. 4,104,190 to Hartshorn discloses a solid composition capable of generating chlorine dioxide when dissolved in water, the solid composition containing sodium chlorite and a chlorine release agent. When dissolved in water, the chlorine species provided by the chlorine release agent reacts with the chlorite to form chlorine dioxide. Suitable chlorine release agents include sodium N-chloro-p-toluenesulfonamide, and sodium dichloroisocyanurate. In an alternate embodiment, a chlorite-free solid composition containing the chlorine release agent may be added to an aqueous solution of stabilized sodium chlorite, as disclosed in U.S. Pat. No. 3,123,521 to Wentworth, et al. In a preferred embodiment, the solid composition also contains an effervescent agent.

Recently, U.S. Pat. No. 4,084,747 to Alliger (U.S. Pat. Re. No. 31,779) proposed the incorporation of lactic acid in an aqueous sodium chlorite composition, the lactic acid lowering the pH of the aqueous media to less than about 7, thereby promoting the formation of chlorine dioxide. It is preferable to form the Alliger composition by admixture of a sodium chlorite-containing and a lactic acid-containing portion within 48 hours of use, for optimum germ-killing effect. To this end, U.S. Pat. No. 4,330,531, also to Alliger, discloses applicators whereby the chlorite portion and the lactic acid portion may be admixed at the time of use. The '531 patent discloses compositions for acne treatment, soaps, and toothpaste.

Another two-part composition is disclosed in Mason, et al., U.S. Pat. No. 4,731,193, which comprises a first part containing stated concentrations of dodecylbenzene sulfonic acid, a phosphate ester, hexamethylene glycol, hydrochloric acid, sodium xylene sulfonate, and water, and a second part containing an aqueous solution of sodium chlorite and sodium xylene sulfonate. The first and second parts are diluted with water.

Kenjo, et al., U.S. Pat. No. 4,731,192, discloses a two-composition cleaning system for contact lenses wherein free oxygen is released when a composition containing a chlorite salt, in aqueous solution, and a solid composition containing solid acid or organic acid salt, an oxygen-consuming agent, and polyvinyl pyrrolidone are combined. Reducing sugars may be included with the solid composition part. Suitable solid acids are tartaric, citric, lactic, malic and gluconic acids.

Quite clearly, the need to admix two parts to achieve a final composition is undesirable. A level of sophistication is needed by the ultimate user, lest incorrectly mixed dosage amounts of the two portions provide too little or too much chlorine dioxide. Alternately, special packaging for mixing aliquot amounts of the two premixes is needed, which special packaging raises the cost of the final product to the ultimate user.

The difficulty in providing a single composition containing sodium chlorite that forms chlorine dioxide when the composition is intended for direct use is that the chlorine dioxide formation heretofore continues unabated. Although the mechanism is not fully understood, it is believed that, at least in part, there is some form of autocatalysis that takes place, with a chloro or oxychloro species first formed continuing the formation of the chlorine dioxide from the sodium chlorite. Alternately, or cooperatively, it is suspected that certain chloro or oxychloro species that are formed acquire sufficient energy levels to activate some type of autocatalytic formation of the chlorine dioxide. Once said activated species is formed, the reaction proceeds accordingly. Whatever the mechanism, the fact remains that compositions containing chlorine dioxide formed in situ from sodium chlorite demonstrate a gradual yet continued reduction in composition pH until substantially all of the sodium chlorite is depleted.

It is an object of the present invention to provide a sodium chlorite-containing composition which releases into the composition levels of chlorine dioxide effective in killing germs and bacteria.

It is a further object of the present invention that in such composition the chlorine dioxide levels obtained achieve an equilibrium concentration, thereby assuring stability over time.

Another object of the present invention is that such composition be complete upon manufacture, there being no necessity to admix other ingredients prior to its use.

Another object of the present invention is to provide compositions wherein there is an excess of sodium chlorite to serve as a source for formation of additional chlorine dioxide, to replace chlorine dioxide diffusing from or otherwise leaving the composition.

These and other benefits and advantages of the present invention will be readily perceived upon a reading of the detailed invention disclosure, a summary of which follows.

SUMMARY OF THE INVENTION

The compositions in accordance with the present invention comprise sodium chlorite, an initiator, and water, the sodium chlorite and initiator each being present in the composition in at last an amount adapted to form interactively an antimicrobially effective concentration of chlorine dioxide in the composition, said composition having a viscosity suitable to suspendably retain the chlorine dioxide in the composition. Suitable as an initiator are hydroxy alkylcelluloses having 2 to about 5 carbons in the alkyl group; alkali metal alginates; xanthan; carrageenan; agar; compounds containing an aldehyde substituent group, including perfumes; perfumes not included in the previous class of aldehydic compounds, and dyes. Mixtures of such initiators may also be used.

Typically, the viscosity of the composition is above about 75 cps., preferably 75 to 1000 cps.

It is believed the initiator interacts with the chlorite ion in the aqueous composition to provide the chlorine dioxide, which interaction apparently ceases when an equilibrium concentration for the chlorine dioxide is reached. Such interactions normally take place within about several days.

The composition preferably has a sodium chlorite concentration of about 0.01 to 1% by weight, while the initiator is typically present at a level above about 0.05%, preferably above about 0.1%. At higher sodium chlorite levels, the time required for interaction becomes increasingly longer. Accordingly, while not excluded herein, such higher sodium chlorite concentrations are not preferred. Because the initiator may provide other properties to the composition, e.g., color, scent, thickening, it may be present at a level in excess of its initiating concentration.

DETAILED DESCRIPTION OF THE PREFERRED EMBODIMENT

Generally, the compositions of the present invention comprise sodium chlorite, an initiator, and water, the composition having a viscosity or a rheology suitable for suspendably maintaining chlorine dioxide within the composition. As hereinafter considered in some detail, it has been found that the materials suitable as an initiator are also suitable to provide other functional attributes to the composition. Accordingly, the initiator (or initiators) may be used in excess so as to provide these other attributes. Moreover, other materials which provide such attributes may also be included in the compositions of the present invention, even though not providing initiation of chlorine dioxide formation.

Compositions of the present invention have a viscosity of above about 75 cps., preferably from about 200 to about 1000 cps. At such viscosity levels, chlorine dioxide, which is formed by interaction between the initiator and the sodium chlorite, is suspendably retained in the composition, that is, diffusion from the composition is slow when the composition is exposed to the atmosphere. It has been found that the formation of chlorine dioxide in the composition reaches an equilibrium or steady-state level. Thus, in an enclosed container, the concentration of chlorine dioxide remains constant when the steady-state level has been reached, while in an open container for the composition (or when the closure for the container is left open), the steady-state level is maintained by formation of additional chlorine dioxide to replace that which diffuses to the atmosphere. Because the chlorine dioxide is highly soluble and because the compositions of the present invention are viscous, the diffusion rate of chlorine dioxide from such open container, however, is quite low. Accordingly, the compositions of the present invention are viewed as being quite stable, inasmuch as the sodium chlorite concentration is generally sufficiently high to operate as a source for the replenishment of chlorine dioxide escaping from the system.

The initially prepared compositions, prior to the formation of chlorine dioxide, comprise an effective level of sodium chlorite, that is, a concentration that is sufficient to form within the composition the aforementioned germicidally effective level of chlorine dioxide. Preferably, the sodium chlorite level is provided in excess, as to provide a source to replace chlorine dioxide leaving the composition. Typically, the sodium chlorite is present in an amount from about 0.01% to about 1.0% by weight of the composition, preferably from about 0.05 to about 0.5%. Other water-soluble chlorite salts may be employed, but are not preferred.

The initiator is present in an amount suitable to interact with the sodium chlorite to form the chlorine dioxide. An excess amount may be used, however, inasmuch as the formation of the chlorine dioxide appears to terminate at an equilibrium concentration. Of course, the equilibrium concentration that is achieved will depend on the precise concentration of each of the constituents in the composition, as well as the composition viscosity and other physical and chemical parameters. The initiator concentration is preferably in excess of that which is initially needed to provide the equilibrium level of the chlorine dioxide, so that additional chlorine dioxide may be formed with the sodium chlorite in the event of chlorine dioxide loss from the composition. An excess of the initiator may also be provided to achieve another desired functional purpose, as discussed below.

Several classes of initiators have been found to be suitable to form chlorine dioxide in the compositions of the present invention, as described below in greater detail. In each class the initiator is believed to interact with the chlorite anion so as to form chlorine dioxide, although the exact mechanism by way of which the chlorine dioxide is formed is not fully understood. The compositions as initially prepared are basic, and although an organic or inorganic acid constituent such as described in the prior art patents is not present, the compositions, after reaching equilibrium, have pH values that are slightly basic, neutral, or somewhat acidic, the pH typically not falling below a value of about 6. It is believed that the initiators herein described effect electron transfer from the chlorite anion to form the chlorine dioxide, but do so at a low rate, possibly through the formation of intermediate reaction products and/or intermediate activation species. The possibility that the initiator somehow autocatalyzes the transformation of the chlorite ion to chlorine dioxide should not be ruled out. That such compositions achieve an equilibrium is surprising and unexpected, as one would expect a shift in the reaction equilibrium towards chlorine dioxide formation at a pH value of less than 8.0.

Suitable initiators are:

(A) Certain materials suitable to thicken aqueous compositions. Such materials are selected from the group consisting of hydroxyalkyl cellulose having 2 to about 5 carbons in the alkyl group and including hydroxyalkyl methyl- and hydroxyalkyl ethylcellulose, alkali metal alginates, xanthan gum, carrageenan, and agar. Quite surprisingly, other materials suitable for functional use as a thickener such as methyl cellulose and sodium carboxymethyl cellulose have been found not to initiate chlorine dioxide formation, but might be incorporated as a thickener or cothickener.

(B) Dyes. The dyes usable in connection with the present invention include many different classes. Thus, it has been found that suitable colorants include Basic Blue No. 1 and Colour Index Dye Nos. 22,610 (Direct Blue 6); 42,045 (Acid Blue No. 1); 42,080 (Acid Blue No. 7); 42,090 (Hidacid Azure Blue); 52,035 (Hidacid Aqua Blue); and 74,180 (Direct Blue 86), which dyes include the phthalocyanine, diazo, thiazine, and triarylmethane classes of dyes. With regard to dyes not specifically referred to herein, potential for use as an initiator may easily be ascertained by routine experimentation, as described in greater detail in the examples below.

(C) Materials including an aldehyde or an acetal substituent group including perfumes containing such groups. Applicant has found that compounds containing an aldehyde group are suitable as initiators. It is believed that the pair of free electrons associated with the oxygen makes the aldehyde substituent group particularly suitable for use as an initiator. Suitable aldehydes include acetaldehyde, propionaldehyde, butyraldehyde and benzaldehyde, as well as aldehydes present in perfumes as a fragrance constituent. Of the latter, mention may be made of aldehydes having from about 5 to about 20 carbons, especially from about 8 to about 16 carbons, including cinnamic aldehyde, decaldehyde, citronellyl oxy-acetaldehyde, cuminic aldehyde, phenol acetaldehyde (monomer), p-methyl hydratropic aldehyde, and cyclamen aldehyde.

(D) Perfumes not including an aldehyde substituent group. Because perfumes are generally mixtures of various materials, the identification of the precise perfume ingredient that causes the formation of chlorine dioxide is more difficult to identify.

Typically, the perfume incorporated in the composition of the present invention is a mixture of organic compounds admixed so that the combined odors of the individual components produce a pleasant or desired fragrance. While perfumes are generally mixtures of variuus materials, individual compounds may also be used as the perfume ingredient, for example, methyl salicylate. The perfume compositions generally contain a main note or the "bouquet" of the perfume composition, modifiers which round off and accompany the main note, fixatives including odorous substances that lend a particular note to the perfume throughout each of the stages of evaporation, substances which retard evaporation, and top notes which are usually low-boiling, fresh-smelling materials.

Perfumery raw materials may be divided into three main groups: (1) the essential oils and products isolated from these oils; (2) products of animal origin; and (3) synthetic chemicals. In addition to aldehyde and acetal substituent groups considered above under (C), these materials include substituent groups, for example, the carbonyl group in ketones; the hydroxyl group in alcohols; the acyl group in esters; the C=O groups in lactones; nitrile groups, and the oxy moiety in ethers, that might be causing the initiation.

The essential oils consist of complex mixtures of volatile liquid and solid chemicals found in various parts of plants. Mention may be made of oils found in flowers, e.g., jasmine, rose, mimosa, and orange blossom; flowers and leaves, e.g., lavender and rosemary; leaves and stems, e.g., geranium, patchouli, and petitgrain; barks, e.g., cinnamon; woods, e.g., sandalwood and rosewood; roots, e.g., angelica; rhizomes, e.g., ginger; fruits, e.g., orange, lemon, and gergamot; seeds, e.g., aniseed and nutmeg; and resinous exudations, e.g., myrrh. These essential oils consist of a complex mixture of chemicals, the major portion thereof being terpenes, including hydrocarbons of the formula $(C_5H_8)_n$ and their oxygenated derivatives. Hydrocarbons such as these give rise to a large number of oxygenated derivatives, e.g., alcohols and their esters, aldehydes and ketones. Some of the more important of these are geraniol, citronellol and terpineol, citral and citronellal, and camphor. Other constituents include aliphatic aldehydes and also aromatic compounds including phenols such as eugenol. In some instances, specific compounds may be isolated from the essential oils, usually by distillation in a commercially pure state, for example, geraniol and citronellal from citronella oil; citral from lemon-grass oil; eugenol from clove oil; linalool from rosewood oil; and safrole from sassafras oil. The natural isolates may also be chemically modified as in the case of citronellal to hydroxy citronellal, citral to ionone, eugenol to vanillin, linalool to linalyl acetate, and safrol to heliotropin.

Animal products used in perfumes include musk, ambergris, civet and castoreum, and are generally provided as alcoholic tinctures.

The synthetic chemicals include not only the synthetically made, also naturally occurring isolates mentioned above, but also include their derivatives and compounds unknown in nature, e.g., isoamylsalicylate, amylcinnamic aldehyde, cyclamen aldehyde, heliotropin, ionone, phenylethyl alcohol, terpineol, undecalactone, and gamma nonyl lactone.

Perfume compositions as received from the perfumery house may be provided as an aqueous or organically solvated composition, and may include as a hydrotrope or emulsifier a surface-active agent, typically an anionic or nonionic surfactant, in minor amount.

The perfume compositions quite usually are proprietary blends of many of the different fragrance compounds. However, one of ordinary skill in the art, by routine experimentation, may easily determine whether such a proprietary perfume blend is suitable to initiate chlorine dioxide formation in the compositions of the present invention, as illustrated in the examples below. Nonaldehydic perfumery constituents found to be suitable include methyl salicylate, amyl salicylate, bornyl acetate and eugenol.

(E) Reducing sugars. It has been found that mono- and disaccharides which are categorized as reducing sugars are suitable for use as initiators in the practice of the present invention. Thus, fructose, glucose, maltose, cellobiose, $\alpha$-lactose and $\beta$-lactose were suitable. Sucrose, a nonreducing sugar, was not. Polysaccharides such as dextran and starch were found to be unsuitable.

The concentration of the initiators (A) through (E) qua initiator is generally low, and an effective amount is generally from about 0.01 to about 2% by weight of the composition, the actual concentration depending on the intrinsic activity of the particular initiator.

Because initiators (A) through (D) also fulfill a functional purpose, they may be incorporated in greater or lesser amount than required for the initiation function. Where less is employed, the difference may be made up by using one or more of the other initiators (A) through (E). Thus, the Group (A) initiator is typically included in an amount of less than about 2% by weight of the composition for initiation, but may be incorporated in an amount of up to 10% by weight of the composition to achieve a desired thickening. The Group (B) initiator may be included in the composition in an amount of less than about 5% by weight of the composition, preferably from about 0.01 to about 0.5%, to provide a desired tinctorial value. The Groups (C) and (D) initiators would be included in an amount of less than about 1% by weight of the composition, preferably from about 0.01 to about 0.25%, to provide a desired fragrance result. Often, when included at a concentration to provide their intended noninitiating function, the total level of the initiators (A), (B), (C) or (D) is in excess of that needed to form chlorine dioxide. However, the additional amount of the initiator does not promote formation of an unwanted level of chlorine dioxide, which achieves an equilibrium at a low concentration. Rather, the additional amount of the initiator is employed functionally to achieve the particular composition property, i.e., viscosity, tint, or scent. Two or more of these initiators may be included in the compositions of the present invention, especially to obtain in concert the effective level for initiation.

The formation of chlorine dioxide commences upon or shortly after admixing of the ingredients, the equilibrium levels generally being reached within a week, preferably within two or three days, of admixture. Suitable equilibrium concentrations of the chlorine dioxide are from about 0.1 to about 10 ppm, preferably 0.1 to 2 ppm, depending upon the ultimate use of the composition. Where the intended utility is disinfection, the equilibrium chlorine dioxide concentration is preferably above about 1 ppm, while when the intended utility is to enhance cleaning and provide some sanitizing effect, the equilibrium chlorine dioxide level is less than about 2 ppm. The amount of chlorine dioxide formed may be controlled by the concentrations of the ingredients, the viscosity of the composition, and by incorporation of an anionic surfactant, which has been found to suppress the conversion of chlorite to chlorine dioxide, possibly by forming a ligand with the chlorite anion. Inclusion of less than about 1% anionic surfactant would be suitable for this purpose.

Other constituents may be incorporated in the compositions of the present invention to provide a particular utility, provided such other constituents are compatible with the formation of the chlorine dioxide and do not themselves deactivate in the compositions. Mention may be made of nonionic surfactants, to provide a cleaning composition.

In preparing the compositions, it is preferred to first form a dilute sodium chlorite premix, which is then thickened with either a noninitiating or a initiating thickener, and then to add in, with stirring, the remaining constituents.

The present invention is illustrated by the examples below.

EXAMPLES

General

In the examples, chlorine dioxide gas is often easily detectable by its characteristic odor. While such sensory evaluations do not indicate the presence of chlorine dioxide, one of several analytical methods was used: (1) spectrophometric measurement of a sample, chlorine dioxide having a peak absorbence of 356 nm, unique among the oxychloro species; (2) titration of an alkaline sample with sodium thiosulfate in the presence of potassium iodide, and (3) purging chlorine dioxide gas from the sample with inert gas and passing the purged gas through a potassium iodide solution.

In the specific examples which follow, all concentrations are reported on an active-ingredient basis, unless otherwise indicated. The perfumes were premixed with the surfactants prior to the addition to the chlorite solution. Except for dye and perfume, all concentrations are reported on an active material basis, by weight percent of the composition.

EXAMPLE 1

Compositions 1-A to 1-E were prepared as indicated below. Commercial sodium chlorite was used, which is 80% active, and contains 5% sodium hydroxide and about 15% sodium chlorite. The sodium chlorite level reported in Table I and throughout these examples is on an active chlorite basis.

TABLE I

| Constituent | Concentration (wt. %) | | | | | | |
|---|---|---|---|---|---|---|---|
| | 1-A | 1-B | 1-C | 1-D | 1-E | 1-F | 1-G |
| Sodium chlorite | 0.24 | 0.24 | 0.24 | 0.24 | 0.24 | 0.32 | 0.32 |
| Methyl cellulose | 1 | | | | | | |
| Sodium carboxymethyl cellulose | | 1 | | | | | |
| Hydroxyethyl cellulose | | | 1 | | | | |
| Hydroxypropyl cellulose | | | | 1 | | | |
| Hydroxybutyl cellulose | | | | | 1 | | |
| Xanthan gum | | | | | | 0.5 | |
| Sodium alginate | | | | | | | 0.5 |
| Water | | | | QS 100% | | | |
| Days observed | 12* | 228 | — | >1 yr | >1 yr | >1 yr | — |
| ClO$_2$ formation | No | No | Yes | Yes | Yes | Yes | Yes* |
| ClO$_2$ present at end of period | No | No | Yes | Yes | Yes | Yes | Yes |
| pH Initial | 9.34 | 9.3 | 9.3 | 9.9 | 9.9 | 9.4 | 9.6 |
| pH at end of period | 9.2 | 9.0 | 5.4 | 7.3 | 7.1 | 7.0 | 7.1 |
| Viscosity (cps. at 20° C.) Initial | — | 884 | 824 | 786 | 404 | 510 | — |
| Viscosity (cps. at 20° C.) Final | — | 165 | 101 | 255 | 150 | 303 | — |

*At 125° F. for 12 days.
**At 180° F. for two hours.

Each of the compositions 1-C through 1-G formed ClO$_2$ within about seven days of preparation. The decrease in viscosity ocurs within about one month before attaining an essentially constant value, as identified above.

EXAMPLE 2 the compositions 2-A through 2-H were prepared.

TABLE II

| Constituent | Concentration (wt. %) | |
|---|---|---|
| | 2-A to 2-G | 2-H |
| Sodium chlorite | 0.16 | 0.16 |
| Carboxymethyl cellulose | 0.80 | 0.80 |
| Dye | 0.05 | — |
| Deionized water | QS 100% | QS 100% |

Compositions 2-A to 2G contained the following dyes:

TABLE III

| Composition | Dye | C.I. No. | Activity (%) |
|---|---|---|---|
| 2-A | Acid Blue No. 1 | 42,045 | 100 |
| 2-B | Direct Blue 86 | 74,180 | 100 |
| 2-C | Acid Blue No. 7 | 42,080 | 100 |
| 2-D | Hidacid Aqua Blue | 52,035 | 91 |
| 2-E | Basic Blue No. 1 | — | 100 |
| 2-F | Acid Blue No. 9 | 42,090 | 89 |
| 2-G | Acid Blue No. 9 and Yellow Dye | 42,090/45,350 | 89/75 |

Each of these compositions was monitored for chlorine dioxide formation. Compositions 2-A and 2-C to 2-G produced chlorine dioxide, while Compositions 2-B and 2-H did not, within 11 days at 125° F. Composition pH, viscosity, and $ClO_2$ concentration were measured initially and at the end of the storage period. The results are provided in Table IV.

TABLE IV

| Composition | First Day $ClO_2$ Observed | Viscosity (cps.) Initial | Viscosity (cps.) Final | pH Initial | pH Final |
|---|---|---|---|---|---|
| 2-A | 7 | 316 | 130 | 9.3 | 6.9 |
| 2-B | None | 300 | 20 | 9.5 | 8.8 |
| 2-C | 7 | 318 | 140 | 9.3 | 6.7 |
| 2-D | 11 | 310 | 135 | 9.4 | 6.9 |
| 2-E | 4 | 312 | 85 | 8.9 | 5.8 |
| 2-F | 7 | 320 | 100 | 9.4 | 6.4 |
| 2-G | 11 | 352 | 80 | 9.4 | 7.1 |
| 2-H | None | 430 | 185 | 9.3 | 9.2 |

EXAMPLE 3

The following Compositions 3-A to 3-J were prepared.

TABLE V

| Constituent | Concentration (wt. %) 3-A to 3-I | Concentration (wt. %) 3-J |
|---|---|---|
| Sodium chlorite | 0.16 | 0.16 |
| Sodium carboxymethyl cellulose | 0.8 | 0.8 |
| Triton X-100[1] | 2 | 2 |
| Perfume (per Table V) | 0.2 | — |
| Deionized water | QS 100 | QS 100 |

[1]Octylphenoxy polyethoxy ethanol (100% active) manufactured by Rohm and Haas Co. Solubilizer for the perfume.

TABLE VI

| Composition | Perfume |
|---|---|
| 3-A | Dragoco 0/710531 |
| 3-B | Florasynth S-1923 |
| 3-C | BBA 860416 |
| 3-D | Florasynth T-4608 |
| 3-E | BBA 871523 |
| 3-F | Dragoco 0/712227 |
| 3-G | Lautier LA 7901946 |
| 3-H | Neutroleum Gamma |
| 3-I | Methyl salicylate |

The Compositions 3-A to 3-J were placed in an oven at 125° F. for 11 days. pH and viscosity measurements were made initially and at the end of 11 days. During the test period, the compositions were monitored for the onset of chlorine dioxide formation. The results are reported in Table VII.

TABLE VII

| Composition | First Day $ClO_2$ Observed | Viscosity at 20° C. (cps.) Initial | Viscosity at 20° C. (cps.) Final | pH Initial | pH Final |
|---|---|---|---|---|---|
| 3-A | 4 | 258 | 160 | 9.2 | 6.5 |
| 3-B | 4 | 268 | 60 | 9.2 | 5.5 |
| 3-C | 4 | 260 | 200 | 9.3 | 6.3 |
| 3-D | 4 | 250 | 30 | 8.8 | 5.7 |
| 3-E | 4 | 266 | 110 | 9.2 | 6.0 |
| 3-F | 4 | 262 | — | 9.3 | — |
| 3-G | 4 | 282 | 170 | 9.2 | 6.2 |
| 3-H | 4 | 482 | 315 | 9.2 | 6.2 |
| 3-I | 4 | 752 | 125 | 8.6 | 6.2 |
| 3-J | None | 440 | 330 | 9.4 | 9.1 |

EXAMPLE 4

Compositions were prepared containing 0.8% sodium chlorite, 4% Triton X-100, 0.25% of a perfume constituent as identified in Table VIII below, and water Q.S. 100%.

TABLE VIII

| Comp. No. | Perfume Component | First Day $ClO_2$ Observed | pH Initial | pH Final |
|---|---|---|---|---|
| 4-A | C-10 aldehyde | 1 | 10.7 | 7.0 |
| 4-B | Methylhexylketone | None after 29 days | 10.8 | 9.7 |
| 4-C | Phenylethyl alcohol | None after 29 days | 10.7 | 9.7 |
| 4-D | Cinnamic aldehyde | 2 | 10.8 | 7.4 |
| 4-E | Amyl salicylate | 7 | 10.5 | 3.9 |
| 4-F | Bornyl acetate | 21 | 10.7 | 6.0 |
| 4-G | Eugenol | 7 | 10.0 | 4.3 |
| 4-H | Acetophenone | None after 30 days | 11.2 | 11.0 |
| 4-J | 80% Dragoco 0/712227 and 20% C-10 Aldehyde | Yes after 1 day | 10.9 | 6.4 |

EXAMPLE 5

Compositions were prepared containing 1.28% sodium chlorite, 0.5% of a saccharide material as identified in Table IX, and water Q.S. 100%.

TABLE IX

| Comp. No. | Perfume Component | First Day $ClO_2$ Observed | pH Initial | pH Final |
|---|---|---|---|---|
| 5-A | Fructose | Yes | 10.1 | 5.7 |
| 5-B | Glucose | Yes | 10.2 | 6.6 |
| 5-C | Maltose | Yes | 10.2 | 6.6 |
| 5-D | Celliobiose | Yes | 10.2 | 6.8 |
| 5-E | α-Lactose | Yes | 10.3 | 6.6 |
| 5-F | β-Lactose | Yes | 10.2 | 6.9 |
| 5-G | Sucrose | No | 10.5 | 10.2 |
| 5-H | Dextran | No | 10.6 | 10.0 |
| 5-I | Starch* | No | 10.8 | 7.3 |

*Present at 2% level.

EXAMPLE 6

The following examples could be prepared to utilize the special properties of a thickened, one-part, chlorine dioxide cleaner.

| Consumer Hand Soap | 0.25% Sodium chlorite |
|---|---|
| | 0.5% Xanthan gum |
| | 1.0% Alpha olefin sulfonate |
| | 0.2% Perfume |
| | 98.05% Water |
| Toilet Bowl Cleaner | 0.25% Sodium chlorite |
| | 0.8% Sodium carboxymethyl cellulose |
| | 0.05% Acid Blue #9 |

| | | |
|---|---|---|
| | 0.20% | Perfume |
| | 3.0% | Sodium sulfate |
| | 95.7% | Water |
| Hard Surface Cleaner | 5.0% | Isopropyl alcohol |
| | 0.25% | Perfume |
| | 0.5% | Triton X-100 |
| | 0.8% | Sodium carboxymethyl cellulose |
| | 0.25% | Sodium chlorite |
| | 93.2% | Water |
| Disinfecting Skin Cream | 2.0% | Lanolin |
| | 0.5% | Hydroxypropyl methyl cellulose |
| | 0.25% | Sodium chlorite |
| | 1.0% | Isopropyl alcohol |
| | 5.0% | Sodium lauryl sulfate |
| | 91.25% | Water |
| Institutional Rinse for Dishwashers (Disinfecting) | 0.5% | Sodium chlorite |
| | 1.5% | Hydroxyethyl cellulose |
| | 2.5% | Isopropyl alcohol |
| | 1.0% | Polyacrylic acid salt |
| | 94.5% | Water |

Several days after preparation, the above compositions would form chlorine dioxide, which would be stably entrapped in the composition.

What is claimed is:

1. A oomposition having an initially basic pH consisting essentially of:
   (1) from about 0.01% to about 1% by weight of sodium chlorite; and
   (2) a chlorine dioxide initiator in an amount suitable to interact with sodium chlorite to form chlorine dioxide selected from the group consisting of: (A) hydroxyalkyl cellulose having from 2 to about 5 carbons in the alkyl group, an alkali metal alginate, xanthan gum, carrageenan, and agar; (B) dyes; (C) compounds having an aldehyde or acetal substituent group; (D) perfumes not including a compound (C), and (E) mono-and disaccharides, and mixtures thereof, said composition forming an antimicrobial concentration of chlorine dioxide of about 0.1 to about 10 ppm equilibrium by interaction of the sodium chlorite and the initiator within a predetermined time subsequent to preparation of the composition and having a viscosity suitable to maintain the chlorine dioxide at a steady-state concentration.

2. The composition of claim 1 further comprising a thickener not suitable for intiating chlorine dioxide formation.

3. The composition of claim 2 wherein said thickener is selected from the group consisting of methyl cellulose and sodium carboxymethyl cellulose.

4. The composition of claim 1 further comprising a colorant not initiating the formation of chlorine dioxide.

5. The composition of claim 1 further comprising a perfume not initiating the formation of chlorine dioxide.

6. The composition of claim 1 wherein sodium chlorite is present in an amount of from about 0.1 to about 1% by weight of the composition.

7. The composition of claim 1 wherein the initiator (A) is present in an amount of from about 0.1 to about 2% by weight of the composition.

8. The composition of claim 1 wherein the initiator (B) is present in an amount of from about 0.01 to about 1% by weight of the composition.

9. The composition of claim 1 wherein the initiator (C) is present in an amount of from about 0.01 to about 1% by weight of the composition.

10. The composition of claim 1 wherein the initiator (D) is present in an amount of from about 0.01 to about 1% by weight of the composition.

11. The composition of claim 1 wherein the initiator (E) is present in an amount of from about 0.01 to about 1% by weight of the composition.

12. The composition of claim 1 wherein the viscosity of the composition is from about 75 to about 1000 cps.

13. The composition of claim 2 wherein the viscosity of the composition is from about 75 to about 1000 cps.

14. The composition of claim 1 wherein the initiator is present in an amount of from about 0.1 to about 2% by weight of the composition.

15. The composition of claim 8 wherein the initiator (B) is a dye selected from the group consisting of Basic Blue No. 1 and Colour Index Dye Nos. 42,045; 42,080; 42,090; 52,035, and 74,180.

16. The composition of claim 9 wherein the initiator (C) is an aldehyde selected from the group consisting of formaldehyde, acetaldehyde, propionaldehyde, cinnimic aldehyde, citronellyl oxy-acetaldehyde, cuminic aldehyde, and cyclamen aldehyde.

17. The composition of claim 10 wherein the initiator (D) is a perfume comprising an essential oil.

18. The composition of claim 10 wherein the perfume comprises a fragrance selected from the group consisting of eugenol, bornyl acetate, salicylate and methyl salicylate, and mixtures thereof.

19. The composition of claim 11 wherein the initiator (E) is selected from the group consisting of glucose, fructose, maltose, celliobiose and lactose.

20. The composition of claim 1 wherein the initiator comprises a mixture of the initiator (C) and the initiator (D).

21. The composition of claim 1 further comprising an anionic surfactant.

* * * * *

UNITED STATES PATENT AND TRADEMARK OFFICE
CERTIFICATE OF CORRECTION

PATENT NO. : 4,861,514
DATED : August 29, 1989
INVENTOR(S) : Richard S. Hutchings It is certified that error appears in the above-identified patent and that said Letters Patent is hereby corrected as shown below:

Column 11:

Claim 1, line 1, after "A," "oomposition" should read --composition--.

Claim 1, line 16, after "ppm," the word --at-- should appear.

Signed and Sealed this

Twenty-third Day of March, 1993

Attest:

STEPHEN G. KUNIN

*Attesting Officer*      Acting Commissioner of Patents and Trademarks